(12) United States Patent
Bonn et al.

(10) Patent No.: US 8,734,857 B2
(45) Date of Patent: May 27, 2014

(54) HYDROLYSATES MADE OF PLANT EXTRACTS AND ANTIBACTERIAL AGENT CONTAINING THE SAME

(75) Inventors: Guenther Bonn, Zirl (AT); Guenther Stecher, Goetzens (AT); Michael A. Popp, Lauf (DE); Robert Mayer, Alpbach (AT)

(73) Assignee: Bionorica SE, Neumarkt (DE)

( * ) Notice: Subject to any disclaimer, the term of this patent is extended or adjusted under 35 U.S.C. 154(b) by 631 days.

(21) Appl. No.: 12/740,396

(22) PCT Filed: Oct. 30, 2008

(86) PCT No.: PCT/EP2008/009171
§ 371 (c)(1),
(2), (4) Date: Sep. 10, 2010

(87) PCT Pub. No.: WO2009/056316
PCT Pub. Date: May 7, 2009

(65) Prior Publication Data
US 2010/0323013 A1    Dec. 23, 2010

(30) Foreign Application Priority Data
Oct. 31, 2007 (DE) .......................... 10 2007 052 223

(51) Int. Cl.
*A61K 36/00* (2006.01)
(52) U.S. Cl.
USPC ........................................................ 424/725
(58) Field of Classification Search
USPC ........................................................ 424/725
See application file for complete search history.

(56) References Cited

U.S. PATENT DOCUMENTS

2007/0196298 A1*  8/2007  Kostick et al. ................. 424/63

FOREIGN PATENT DOCUMENTS

CN    1986539 A  *  6/2007

OTHER PUBLICATIONS

Brønnum-Hansen et al. Anthocyanin Colorants From Elderberry (*Sambucus nigra* I.) IV Further Studies on Production of Liquid Extracts, Concentrates and Freeze Dried Powders; Journal of Food Technology (1986), 21, pp. 605-614.*

* cited by examiner

*Primary Examiner* — Patricia Leith
(74) *Attorney, Agent, or Firm* — Novak Druce Connolly Bove + Quigg LLP

(57) ABSTRACT

The present invention relates to an antibacterial agent and a hydrolysate made of at least one extract that has been produced by extraction using ethanol/water from dried plant material of: a) at least one of the plants selected from the group consisting of: *Verbena officinalis* L., *Sambucus nigra* L., *Primula veris* L., *Primula elatior* (L.) Hill, and *Gentiana lutea* L.; and a mixture thereof; or b) a mixture of: *Verbena officinalis* L., *Sambucus nigra* L., *Primula veris* L., *Gentiana lutea* L., and Rumicis herba; and subsequent removal of the ethanol/water extraction agent, wherein the hydrolysate can be obtained from the extract via hydrolytic treatment using a mineral acid. The hydrolyzates according to the invention show a pronounced antibacterial effect against germs relevant to the skin, ears, nose, and throat and respiratory systems.

18 Claims, No Drawings

HYDROLYSATES MADE OF PLANT EXTRACTS AND ANTIBACTERIAL AGENT CONTAINING THE SAME

The present invention relates to a hydrolysate made of at least one extract from at least one plant material according to the preamble of claim 1 and to an antibacterial agent.

Extracts from the five indigenous medicinal plants:
Rumicis herba (*Rumex acetosa* L., *Rumex acetosella* L., *Rumex obtusifolius* L., *Rumex patientia* L., and *Rumex crispus* L.);
*Verbena officinalis* L.;
*Sambucus nigra* L.;
*Primula veris* L. and *Primula elatior* (L.) Hill; and
*Gentiana lutea* L.

together have been known for more than 70 years as secretolytic agents for infections of the upper respiratory tracts, and specifically sinusitis under the brand name of SINUPRET® (registered trademark of BIONORICA).

Each individual drug contributes a part to the unique efficacy of the composition:

From *Gentiana lutea* (Yellow Gentian), typically the root is used for medicinal purposes. The ingredients which have an expectorant effect also include several secoiridoid glycosides.

In Rumicis Herba (sorrel herb), the active ingredients from the leaves and stems have an expectorant and an anti-inflammatory effect and a positive influence on the body's own defense mechanisms. Ingredients include, for example, flavonoids, oxalic acid and different tannins.

*Verbena officinalis* (Common Verbena) has an expectorant and an antiviral effect. The main ingredients of the medicinally used leaves and stems include iridoid glycosides, cinnamic acid glycosides, and flavonoids.

From *Sambucus nigra* (Black Elder), the blossoms are used and the ingredients thereof have an expectorant effect. The ingredients include different flavonol glycosides and sambunigrin as the main active ingredient, a cyanogenic glycoside, which has an antiviral effect.

The active ingredients from the blossoms and capsules of *Primula veris* (Cowslip) and/or *Primula elatior* (L.) Hill (True oxlip) fight viruses and have an expectorant effect. The ingredients include triterpene saponins and phenol glycosides, such as primulaverin. *Primula veris* and/or *Primula elatior* act as mild secretolytic agents and expectorants for the treatment of respiratory tract diseases.

By combining these five medicinal plants, a composition is obtained, which can be used to achieve sufficient effects for medicinal purposes. The composition is preferably used for infections of the ear-nose-throat region and is specially suited for treating acute and chronic sinusitis.

Sinusitis can occur in acute or chronic form. Both forms are frequent, wherein in three out of four cases sinusitis develops as a result of an infection of the mucous membrane from a head cold spreading to the paranasal sinuses.

The paranasal sinuses are part of the upper respiratory tract. The respiratory tract extends from the primary nasal cavity with the different sinuses to the alveoli. The paranasal sinuses include the frontal sinuses, the ethmoidal air cells, the sphenoidal sinuses, and the maxillary sinuses. All bony cavities mentioned above are lined on the insides with mucous membranes and open into the primary nasal cavity through narrow openings, referred to as ostia.

Dirt particles and pathogens, such as viruses and bacteria which enter with the respiratory air, adhere to the protective mucous covering the surface of the respiratory tracts and are attacked and rendered harmless by the antibodies present in the mucous. In order to allow foreign bodies to be flushed out of the body, the mucous must be transported with the help of the cilia of the ciliated epithelium in the direction of the pharynx, where it can be swallowed.

In order to be able to fend off infection-related respiratory tract diseases, the mucous membrane must have unimpaired protective and cleaning mechanisms at its disposal. For this purpose, it is indispensable, when removing the mucous loaded with pathogenic agents that the cilia can work without impairment and, through the wavy movements thereof, can transport the mucous and that the mucous is fresh and has low viscosity.

During an infection, the protective and cleaning mechanisms of the mucous membrane are not longer fully functional.

Viruses such as rhinoviruses, adenoviruses or coronaviruses trigger inflammatory reactions of the mucous membranes, thereby causing the mucous membrane to swell and produce an increased amount of mucus. The result is first a watery, later a viscous mucus flow. During the course of the inflammation of the nasal mucosa, the ostia of the sinuses can swell shut and mucus can no longer flow into the nose. This creates congestion in the sinuses. In the viscous mucus, the cilia can no longer move and stick together. The cleaning mechanism of the mucous membrane does not function any more.

In such an environment marked by viscous mucus, the ubiquitously present bacteria fell particularly well. The mucus constitutes an optimal culture medium for bacteria, where they can rapidly multiply.

In this way, acute sinusitis is the result of an initially simple cold in three out of four cases.

If these unfavorable conditions, such as a swollen mucous membrane and sticky cilia due to viscous mucus, last for a longer period, the result can be chronic sinusitis, which can permanently damage the mucous membrane and cilia.

ENT-relevant pathogenic agents settling into the mucus include, for example, *Staphylococcus aureus, Staphylococcus epidermidis, Streptococcus pyogenes, Streptococcus pneumoniae* or *Haemophilus influenzae.*

Among them is also a *Staphylococcus aureas* strain that is resistant to methicillin, called MRSA. Standard antibiotics such as β-lactam antibiotics, for example oxacillin, penicillin and amoxicillin, no longer have an effect on this bacterium, because the excessive use of antibiotics, which do not fully destroy the pathogenic agents, have created resistivity. These germs represent an additional risk in surgical intensive care units, where they can cause pneumonia, wound infections, and blood poisoning.

The ground raw drugs and ethanolic/aqueous extracts, or the dry extracts produced therefrom (produced, for example, by withdrawing the solvent/extracting agent at reduced pressure) made of *Gentiana lutea*, Rumicis herba, *Verbena officinalis, Sambucus nigra*, and *Primula veris* are already used in the pharmaceutical product Sinupret® (as extract: in the formulation as drops; and as coated tablets containing the ground raw drugs) from BIONORICA as a secretolytic agent and has been successfully applied due to the exclusively plant-based healing power.

The medicinal plants used in Sinupret® are carefully selected, analyzed, and processes. BIONORICA achieves the consistent quality of the pharmaceutical product by employing optimally developed cultivation and harvest strategies and extremely stringent quality control.

In the event of an obstruction of the upper respiratory tract by viscous mucus, the ingredients of the composition used (*Gentiana lutea*:Rumicis herba:*Verbena officinalis:Sambucus nigra:Primula veris*=1:3:3:3:3) stimulates the formation of fresh, low-viscosity mucus. In this way, the accumulated mucus can be dissolved and discharged in the direction of the pharyngeal space. The inflammation of the nasal mucosa decreases, thereby causing the mucous membrane to go down and the sinuses to open. In this way, Sinupret® gently restores the self-cleaning force of the respiratory tract. One characteristic of Sinupret® is the good compatibility thereof, wherein the dosage determined by BIONORICA rarely produces side effects in the patient and no interactions with other pharmaceutical drugs are known.

The main active ingredient in *Sambucus nigra*, the cyanogenic glycoside sambunigrin, has an antiviral effect, which can be attributed to the fact that it covers the spikes of the flu viruses, by which they can penetrate cells and trigger infections, and blocks them (Grabovac, A. and Ullmer, A., Österreichische Apotheker-Verlagsgesellschaft m.b.H., 2003).

The German patent specification DE 10 2005 053 926 B3 describes a topical antibacterial effect of the above-mentioned individual drugs and the drug mixture.

This effect was surprising to the professional world, because it was believed until then that extracts from Rumicis herba, *Verbena officinalis, Sambucus nigra*, and *Primula veris* exhibit only secretolytic, but not antibacterial effects.

In addition, it is known from the German patent application DE 103 41 579 A1 relating to *Gentiana lutea* extracts that they exhibit an antibacterial effect.

While in both cases, there is a clinically highly interesting spectrum of efficacy against a plurality of clinically relevant germs, the necessary dosages are at times not very practical.

Proceeding from the prior art disclosed in DE 10 2005 053 926 B43 of the Sinupret® composition, it is therefore the object of the present invention to provide a material which exhibits improved antibacterial efficacy.

The above object is achieved by the characterizing features of claims 1 and 18.

The invention relates in particular to a hydrolysate made of at least one extract, which is produced by extraction using ethanol/water from dried plant material:

a) at least one of the plants, selected from the group consisting of: *Verbena officinalis* L., *Sambucus nigra* L., *Primula veris* L., *Primula elatior* (L.) Hill and *Gentiana lutea* L.; and a mixture thereof; or b) a mixture of: *Verbena officinalis* L., *Sambucus nigra* L., *Primula veris* L., *Gentiana lutea* L. and Rumicis herba; and subsequent removal of the ethanol/water extraction agent, wherein the hydrolysate can be obtained from the extract by way of hydrolytic treatment using a mineral acid.

A preferred hydrolysate is characterized in that the extracts can be produced from the plant material using an extraction agent made of 50% by volume ethanol and 50% by volume water over 24 hours while stirring and subsequent vacuum evaporation of the solvent.

A further preferred embodiment of the invention is a hydrolysate which can be obtained by the hydrolytic treatment of the plant extracts with hydrochloric acid as the mineral acid, in particular hydrochloric acid having a concentration of 1 M to 10 M, preferably 6 to 9 M, in particular approximately 8 M, at 80° C. to 100° C., particularly approximately 90° C., for 30 minutes to 120 minutes, in particular 40 minutes to 60 minutes, preferably approximately 45 minutes.

It is preferred to carry out the hydrolytic treatment of the extracts in the presence of ethanol, in particular ethanol diluted with water, preferably 50% by volume ethanol.

In order to ensure that the hydrolysates of the present invention have good physiological compatibility, the extracts are evaporated to dryness after the acid treatment step, placed preferably in water, a buffer, or in diluted ethanol, and optionally neutralized with a pharmaceutically acceptable alkali. Possible alkalis are, for example, NaOH, $Na_2CO_3$ or $Na_2HPO_4$.

The hydrolysate is preferably produced from an extract stemming from the following plant components:
Rumicis herba (*Rumex acetosa* L., *Rumex acetosella* L., *Rumex obtusifolius* L., *Rumex patientia* L. and *Rumex crispus* l.): leaves and stems
*Verbena officinalis*: leaves and upper stem sections
*Sambucus nigra*: blossoms
*Primula veris* and/or *Primula eliator*: blossoms and capsules
*Gentiana lutea*: roots.

Particularly preferred is a hydrolysate made of an extract of a mixture of:
*Gentiana lutea*: roots;
Rumicis herba: leaves and stems;
*Verbena officinalis*: leaves and upper stem sections;
*Sambucus nigra*: blossoms; and
*Primula veris*: blossoms and capsules;
wherein the individual drugs are present in the extract to be hydrolyzed in particular in a mass ratio of 1:1:1:1:1 to 1:3:3:3:3.

It came as a complete surprise when it was found that the hydrolysates according to the invention exhibit an antibacterial effect.

The hydrolysates of the present invention generally have a significant antibacterial effect, which in the scope thereof is comparable to an antibiotic control agent made of amoxicillin and clavulanic acid (mass ratio of 6:1). In contrast, non-hydrolytically treated pure extract exhibit only a low to no antibacterial activity in the test system used.

The hydrolysates of the present invention can be used to produce agents having an antibacterial effect against skin and respiratory tract relevant bacteria, in particular gram positive cocci, especially *Staphylococcus aureus, Staphylococcus epidermidis, Streptococcus pyogenes, Streptococcus pneumoniae, Streptococcus mutans* and/or gram negative rod bacteria, in particular *Haemophilus influenzae*.

The hydrolysates were tested within the context of the present invention against the following skin, ENT and respiratory tract relevant pathogenic agents and found to be effective: *Staphylococcus aureus* (ATCC 25923), *Staphylococcus epidermidis* (ATCC 12228), *Streptococcus pneumoniae* (DSMZ 20566), *Streptococcus pyogenes* (DSMZ 20565), *Streptococcus mutans* (ATCC 35668), *Haemophilus influenzae* (DSMZ 4690), *Klebsiella pneumoniae* (ATCC 13883), and *Enterococcus casseliflavus* (VRE) (DSMZ 20680) as well as, against intestinal bacteria, *Escherichia coli* (ATCC 25922) and *Enterococcus faecalis* (VRE) (ATCC 19433).

The hydrolysates of the present invention can advantageously and in manners which are known for producing an antibacterial agent. Such antibacterial agents can be used for the protection against and/or treatment of infections, or topically on the skin and mucous membranes in the form of a galenic formulation that corresponds to the applications thereof.

The galenic formulations of the hydrolysates/antibacterial agents of the present invention are characterized in that the oral formulations comprises sugar-coated tablets, tablets, film-coated tablets, powders, capsules, or liquid dilutions, in particular drops, oral solutions or syrups.

When used for topical applications, in particular sprays, ointments, emulsions, powders, liquid or solid preparations for inhalation, compresses, wound and gum dressings, tamponades, tonsil brush solutions, gargling solutions, or rinsing solutions for the nose and ears are suited.

The tamponades mentioned above are also suited for dental applications.

In order to use the hydrolysates according to the invention as rinsing solutions for the nose and ears, they are advantageously used in combination with physiological or hyperosmolar concentrations of salts or salt mixtures.

For the use as an antibacterial agent, it has been found that a preparation present as a lyophilisate has many advantages, these being in particular storage and long-term stability.

The antibacterial agents of the present invention can, of course, contain the pharmaceutically customary adjuvants.

During microbiological analyses conducted at the Institute for Analytical Chemistry and Radiochemistry at the University of Innsbruck, it was surprisingly found that the hydrolysates according to the invention have a broad, in part pronounced antibacterial effect against skin, respiratory tract and ENT-relevant pathogenic agents, which in corresponding tests with respect to the antibacterial effect were considerably more pronounced than was the case of non-hydrolyzed extracts. For example, antibacterial sensitivity tests using the agar diffusion test according to Mueller-Hinton [Mueller, H. J. and Hinton, J. (1941): A protein-free medium for primary isolation of the Gonococcus and Meningococcus. Proc. Soc. Expt. Biol. Med.; 48:330-333] showed that out of the five non-hydrolyzed individual drug extracts only Rumicis herba and *Primula veris* were effective against multiple pathogenic agents, and that the non-hydrolyzed mixture of *Gentiana lutea, Sambucus nigra, Verbena officinalis,* Rumicis herba, and *Primula veris* surprisingly showed practically no antibacterial effect against the bacteria reference panel tested in the agar diffusion test. Interestingly, the same findings, that is, that the antibacterial effect is aimed at one germ at most, was also found for the different combinations of at least three individual drugs among the five that are mentioned.

This is analogous to the German patent specification DE 10 2005 053 926 B3, which indicates that the antibacterial effect of non-hydrolyzed individual drugs or combinations thereof can likewise only be observed for just a few germs. With respect to the pathogenic agents which exhibited an effect for the non-hydrolyzed extracts and the extent of the effect there is broad agreement between the prior art and the present invention.

Initially, the finding that, after hydrolysis of the extracts of the individual drugs, the antibacterial effects thereof were in part reversed was all the more surprising: For example, a hydrolyzed extract according to the invention made of Rumicis herba practically exhibited no antibacterial activity any more, while the non-hydrolyzed extract had previously exhibited the most pronounced effect against most of the bacterial strains that were tested.

The biggest surprise, however, was that a hydrolysate made of a mixture of *Gentiana lutea, Sambucus nigra, Verbena officinalis, Primula veris,* and Rumicis herba exhibits a significant antibacterial effect against all bacterial strains that were tested.

The hydrolysates and the antibacterial agent of the present invention can therefore advantageously be used for the treatment of infections triggered by respiratory tract-relevant pathogenic agents. The expectorant and anti-inflammatory effects of the analyzed drugs and drug mixtures were supplemented by the additional antibacterial effect, whereby an infection of the upper respiratory tracts is not only reduced by dissolving the viscous, pathogen-loaded mucus, but is completely eliminated by destroying the bacterial pathogenic agents.

Due to the medicinal effect on the basis of the five medicinal plants, that is *Gentiana lutea,* Rumicis herba, *Verbena officinalis, Sambucus nigra,* and *Primula veris,* a patient suffering from sinusitis will receive gentle treatment without synthetic-chemical components. In addition, the preparation is marked by good compatibility with respect to the interactions thereof with other drugs and with respect to side effects, which rarely occur.

The antibacterial agent of the present invention is effective in particular against the following pathogenic agents, exhibiting antibacterial efficacy in particular against gram positive cocci such as *Staphylococcus aureus, Staphylococcus epidermidis, Streptococcus pyogenes, Streptococcus pneumoniae,* and against gram negative rod-shaped bacteria such as *Klebsiella, Haemophilus influenzae, Pseudomonas aeruginosa* as well as against Enterobacteriaceae *faecalis* (VRE), Enterobacteriaceae *casseliflavus* and *E. coli.*

As a result, the present invention also relates to the use of the hydrolysates and antibacterial agents according to the invention for producing a pharmaceutical product for the treatment of infections of the respiratory tract and ENT space triggered by respiratory tract and ENT-relevant pathogenic agents.

Additional advantages and characteristics of the present invention will be apparent from the description of the exemplary embodiments.

EXAMPLES

Production of the Plant Extracts

The individual drugs *Gentiana lutea,* Rumicis herba, *Verbena officinalis, Sambucus nigra,* and *Primula veris* as well as mixed extracts thereof having variable drug compositions (5-plant extract, 4-plant extract, 3-plant extract) were extracted in 50% EtOH/$H_2O$ (v/v, approx. 1 g plant material for 20 ml solvent) for 24 hours at room temperature while stirring. For the mixed extracts, this means that from each plant, as stated above, approximately 1 g of material was used, wherein such a material mixture was extracted with a total of 20 ml of solvent. The mass ratio of the individual drugs was 1:1:1:1:1, 1:1:1:1, 1:1:1.

Production of the Hydrolysates 1.6 ml of the above-described extracts was mixed with 320 µl of 25% HCl (corresponds to 8.1 mol/L) and 80 µl 50% EtOH and hydrolyzed for 45 minutes at 90° C.

For comparison purposes, in a second step, the hydrolysis was conducted with 1 ml extract under the same conditions, while adding 1 ml 25% HCl.

After concentrating the extracts by evaporation, the residue was placed in 1 ml sterile water, and the test solution obtained in this way was tested for the antibacterial effect thereof.

The effects of the hydrolysates were compared to the effects of the individual or mixed extracts prior to hydrolysis. Non-hydrolyzed extracts were present in 50% EtOH/$H_2O$ (see above), wherein optionally by evaporation the concentrations of the ingredients of the non-hydrolyzed and hydrolyzed extracts were aligned with each other. As a result, the extracted ingredients were present in the same volumes when the same masses of plant drugs were used.

Analysis of the Antibacterial Effect Before and after Hydrolysis of the Plant Extracts Screening Method:

80 µl of the test solution (non-hydrolyzed or hydrolyzed) was placed on Müller Hinton agar plates or Müller Hinton Agar plates with 5% sheep blood containing an unknown concentration of the bacteria to be tested and incubated for 24 hours at 37° C. Spiral platter:

A bacteria colony was suspended in 5 ml CASO-Bouillon and incubated for 24 hours at 37° C.

The supernatant was removed after centrifuging the sample, washed with 0.9% NaCl, and diluted to a concentration of $10^7$ cfu/ml (colony forming unit per milliliter).

Also 80 µl test solution (non-hydrolyzed or hydrolyzed) was diluted 1:2, 1:20 and 1:200 and mixed with the bacteria suspension (for Pneumococcus and *H. influenzae:* 1:10, for the remaining pathogens 1:100). 0.9% NaCl was used for positive control purposes.

The samples are plated with a Whitley Automatic Spiral Platter (WASP) after 0.4 and 8 hours and incubated for 24 hours at 37° C.

Before Hydrolysis:
Screening Tests: Individual Drugs/Mixed Extracts Before Hydrolysis

TABLE 1

Results of the analysis for antibacterial effects of the individual extracts

|  | Gentiana l. | Sambucus n. | Verbena o. | Rumicis h. | Primula v. | 5-plant extract |
|---|---|---|---|---|---|---|
| *Staph. aureus* | Ø | Ø | Ø | + | +M | Ø |
| *P. aeruginosa* | Ø | +B | Ø | +B | Ø | Ø |
| Pneumococcus | Ø | Ø | Ø | +M | +M | Ø |
| *Strept. pyogenes* | Ø | Ø | Ø | +M | +M | Ø |
| *Klebsiella* | Ø | Ø | Ø | Ø | Ø | Ø |
| *E. coli* | Ø | Ø | Ø | Ø | Ø | Ø |
| *H. influenzae* | Ø | Ø | Ø | Ø | Ø | Ø |
| *Staph. epidermidis* | Ø | Ø | Ø | + | Ø | Ø |
| *Ent. faecalis* (VRE) | Ø | Ø | Ø | + | Ø | Ø |
| *Ent. casseliflavus* (VRE) | Ø | Ø | Ø | +M | Ø | Ø |

*Gentiana lutea* (Gentians l.), *Sambucus nigra* (Sambucus n.): *Verbena officinalis* (Verbena o.), *Rumex herba* (Rumex h.) and *Primula veris* (Primula v.) as well as a mixed extract made of all 5 plants (5-plant extract) against the pathogens *Staphylococcus aureus* (Staph. aureus)(ATCC 25923), *Pseudomonas aeruginosa* (P. aeruginosa)(ATCC 27853), *Streptococcus pneumoniae* (Pneumococcus)(DSMZ 20566), *Streptococcus pyogenes* (Strept. pyogenes)(DSMZ 20565), *Klebsiella pneumoniae* (Klebsiella) (ATCC 13883), *Escherichia coli* (E. coli)(ATCC 25922), *Haemophilus influenzae* (H. influenzae) (DSMZ 4690), *Staphylococcus epidermidis* (Staph. epidermidis) (ATCC 12228), *Enterococcus faecalis* (VRE) (Ent. faecalis (VRE) (ATCC 19433)) and *Enterococcus casseliflavus* (VRE) (Ent. casseliflavus (VRE) (DSMZ 20680)).
+M = antibacterial effect on Mueller Hinton Agar; +B = antibacterial effect on Mueller Hinton Agar with 5% sheep blood, + = effect on both plates Spiral Platter: Rumicis Herba, Before Hydrolysis

TABLE 2

Quantification of the antibacterial effect of *Rumicis herba* and *Primula veris* against the pathogens mentioned in Table 1 using spiral plating.

|  | Rumicis h. | | Primula v. | |
|---|---|---|---|---|
|  | 1:20 | 1-200 | 1:20 | 1-200 |
| *Staph. aureus* | +++ | + | ++ | (+) |
| *P. aeruginosa* | Ø | Ø | Ø | Ø |
| Pneumococcus | ++++ | ++++ | ++++ | ++++ |
| *Strept. pyogenes* | ++++ | ++++ | ++++ | ++ |
| *Klebsiella* | Ø | Ø | Ø | Ø |
| *E. coli* | Ø | Ø | Ø | Ø |
| *H. influenzae* | Ø | Ø | Ø | Ø |
| *Staph. epidermidis* | ++ | ++ | Ø | Ø |
| *Ent. faecalis* (VRE) | ++++ | ++++ | Ø | Ø |
| *Ent. casseliflavus* | ++++ | ++++ | Ø | Ø |

The samples were quantified in 1:20 and 1:200 dilutions.
++++ = $10^2$ cfu/ml after 0 h, +++ = $10^2$ cfu/ml after 4 h, ++ = $10^2$ cfu/ml after 8 h, + = $10^3$-$10^4$ cfu/ml after 8 h, (+) = higher activity compared to control group Screening Tests: Plant Mixtures in Different Compositions, Non-Hydrolyzed

TABLE 3

From the individual drugs mentioned in Table 1, 50% ethanolic mixed extracts comprising 5, 4 or 3 plants were produced and analyzed for the antibacterial effects thereof against the pathogens mentioned in Table 1 in screening tests.

|  | RGVS | RVSP | RGVP | RGSP | RGVS | GVSP | RVP | VSP | GVP | GVSP | RS |
|---|---|---|---|---|---|---|---|---|---|---|---|
| *Staph. aureus* | Ø | + | + | + | (+) | (+) | Ø | Ø | Ø | Ø | (+) |
| *P. aeruginosa* | Ø | Ø | Ø | Ø | Ø | Ø | Ø | Ø | Ø | Ø | Ø |
| Pneumococcus | Ø | Ø | Ø | Ø | Ø | Ø | (+) | Ø | Ø | Ø | Ø |
| *Strept. pyogenes* | Ø | Ø | Ø | Ø | Ø | Ø | Ø | Ø | Ø | Ø | + |
| *Klebsiella* | Ø | Ø | Ø | Ø | Ø | Ø | Ø | Ø | Ø | Ø | Ø |
| *E. coli* | Ø | Ø | Ø | Ø | Ø | Ø | Ø | Ø | Ø | Ø | Ø |
| *H. influenzae* | Ø | Ø | Ø | Ø | Ø | Ø | Ø | Ø | Ø | Ø | Ø |
| *Staph. epidermidis* | Ø | Ø | Ø | Ø | Ø | Ø | Ø | Ø | Ø | Ø | Ø |
| *Ent. faecalis* (VRE) | Ø | Ø | Ø | Ø | Ø | Ø | Ø | Ø | Ø | Ø | Ø |
| *Ent. casseliflavus* (VRE) | Ø | Ø | Ø | Ø | Ø | Ø | Ø | Ø | Ø | Ø | Ø |

|  | RGP | RGS | RGV | RVS | GSP |
|---|---|---|---|---|---|
| *Staph. aureus* | + | Ø | Ø | Ø | Ø |
| *P. aeruginosa* | Ø | Ø | Ø | Ø | Ø |
| Pneumococcus | Ø | Ø | Ø | Ø | Ø |
| *Strept. pyogenes* | Ø | + | Ø | Ø | Ø |
| *Klebsiella* | Ø | Ø | Ø | Ø | Ø |
| *E. coli* | Ø | Ø | Ø | Ø | Ø |

TABLE 3-continued

From the individual drugs mentioned in Table 1, 50% ethanolic mixed extracts comprising 5, 4 or 3 plants were produced and analyzed for the antibacterial effects thereof against the pathogens mentioned in Table 1 in screening tests.

| | | | | | |
|---|---|---|---|---|---|
| H. influenzae | ∅ | ∅ | ∅ | ∅ | ∅ |
| Staph. epidermidis | ∅ | ∅ | ∅ | ∅ | ∅ |
| Ent. faecalis (VRE | ∅ | ∅ | ∅ | ∅ | ∅ |
| Ent. casseliflavus (VRE) | ∅ | ∅ | ∅ | ∅ | ∅ |

*Gentiana lutea* (G), *Sambucus nigra* (S), *Verbena officinalis* (V), *Rumicis herba* (R), and *Primula veris* (P).
+ = effect on both plates (Müller Hinton Agar, Müller Hinton Agar with 5% sheep blood), (+) = effect on one plate After Hydrolysis:
Screening Tests: Individual Drugs/Mixed Extracts after Hydrolysis

TABLE 4

The extracts obtained of the plant drugs mentioned in Table 1 as well as a mixed extract comprising all five plants was hydrolyzed using hydrochloric acid and tested for the antibacterial effect against the pathogens listed in Table 1.

| | *Gentiana l.* | *Sambucus n.* | *Verbena o.* | *Rumicis h.* | *Primula v.* | 5-plant extract |
|---|---|---|---|---|---|---|
| *Staph. aureus* | + | + | ∅ | ∅ | + | + |
| *P. aeruginosa* | + | (+) | ∅ | ∅ | + | + |
| Pneumococcus | + | + | + | ∅ | + | + |
| *Strept. pyogenes* | + | + | + | ∅ | + | + |
| *Klebsiella* | + | (+) | ∅ | ∅ | + | + |
| *E. coli* | + | ∅ | ∅ | ∅ | + | + |
| *H. influenzae* | + | + | ∅ | ∅ | + | + |
| *Staph. epidermidis* | + | + | + | ∅ | + | + |
| *Ent. faecalis* (VRE) | + | ∅ | ∅ | ∅ | + | + |
| *Ent. casseliflavus* (VRE) | + | ∅ | ∅ | ∅ | + | + |

After the hydrolysis was conducted, the extracts were evaporated to dryness and dissolved in sterile water.
+M = antibacterial effect on Mueller Hinton Agar; + = effect on both plates (Müller Hinton Agar, Müller Hinton Agar with 5% sheep blood), (+) = effect on one plate Spiral Platter: Quantification of the Individual Drugs or the 5-Plant Extract

TABLE 5

Quantification of the hydrolysates obtained for the plant drugs mentioned in Table 1 as well as the 5-plant extract against the pathogens listed in Table 1 using a spiral platter.

| | *Gentiana l.* | *Sambucus n.* | *Verbena o.* | *Primula v.* | 5-plant extract |
|---|---|---|---|---|---|
| *Staph. aureus* | (+) | (+) | + | +++ | (+) |
| *P. aeruginosa* | ++++ | +++ | ++++ | ++++ | ++++ |
| Pneumococcus | +++ | + | (+) | ++++ | |
| *Strept. pyogenes* | ++++ | ++++ | ++++ | ++++ | ++++ |
| *Klebsiella* | +++ | ++ | ++ | +++ | +++ |
| *E. coli* | +++ | (+) | (+) | + | + |
| *H. influenzas* | ++++ | ++++ | ++++ | ++++ | ++++ |
| *Staph. epidermidis* | +++ | +++ | +++ | ++++ | +++ |
| *Ent. faecalis* (VRE) | +++ | ++ | + | +++ | +++ |
| *Ent. casseliflavus* (VRE) | +++ | ++ | +++ | +++ | +++ |

All solutions were measured in 1:20 dilutions.
++++ = 102 cfu/ml after 0 h, +++ = $10^2$ cfu/ml after 4 h, ++ = $10^2$ cfu/ml after 8 h, + = $10^3$-$10^4$ cfu/ml after 8 h, (+) = higher activity compared to control group Comparison of the Reproducibility of the Antibacterial Effect

TABLE 6

Study regarding the reproducibility of the antibacterial effect of several extracts of the same individual drugs (Sambucus nigra, Gentiana lutea, Primula veris).

| Sambucus n. | Extract 1 | Extract 2 | Extract 3 |
|---|---|---|---|
| Staph. aureus | (+) | (+) | (+) |
| P. aeruginosa | +++ | +++ | ++++ |
| Pneumococcus | + | ++ | ++ |
| Strept. pyogenes | ++++ | +++ | +++ |
| Klebsiella | ++ | (+) | +++ |
| E. coli | (+) | (+) | |
| H. influenzae | ++++ | ++++ | |
| Staph. epidermidis | +++ | ++ | ++++ |
| Ent. faecalis (VRE) | ++ | (+) | ++ |
| Ent. casseliflavus (VRE) | ++ | ++ | +++ |

| Gentiana l. | Extract 1 | Extract 2 | Extract 3 |
|---|---|---|---|
| Staph. aureus | (+) | (+) | (+) |
| P. aeruginosa | ++++ | ++++ | ++++ |
| Pneumococcus | +++ | ++++ | ++++ |
| Strept. pyogenes | ++++ | ++++ | ++++ |
| Klebsiella | +++ | +++ | ++++ |
| E. coli | +++ | + | ++++ |
| H. influenzae | ++++ | ++++ | ++++ |
| Staph. epidermidis | +++ | +++ | ++++ |
| Ent. faecalis (VRE) | +++ | ++ | +++ |
| Ent. casseliflavus (VRE) | +++ | +++ | ++++ |

| Primula v. | Extract 1 | Extract 2 | Extract 3 | Extract 4 | Extract 5 |
|---|---|---|---|---|---|
| Staph. aureus | +++ | (+) | ++ | (+) | + |
| P. aeruginosa | ++++ | +++ | ++++ | ++++ | ++++ |
| Pneumococcus | ++++ | (+) | +++ | +++ | +++ |
| Strept. pyogenes | ++++ | +++ | ++++ | ++++ | +++ |
| Klebsiella | +++ | (+) | ++++ | + | +++ |
| E. coli | + | (+) | +++ | ++ | + |
| H. influenzae | ++++ | +++ | ++++ | ++++ | ++++ |
| Staph. epidermidis | ++++ | (+) | +++ | +++ | +++ |
| Ent. faecalis (VRE) | +++ | (+) | +++ | + | + |
| Ent. casseliflavus | +++ | ++ | +++ | +++ | ++ |

Quantification using spiral platter in 1:20 dilution of the sample.
++++ = $10^2$ cfu/ml after 0 h, +++ = $10^2$ cfu/ml after 4 h, ++ = $10^2$ cfu/ml after 8 h, + = $10^3$-$10^4$ cfu/ml after 8 h, (+) = higher activity compared to control group

The invention claimed is:

1. A hydrolysate prepared by:
   a) Extracting dried plant material, wherein the dried plant material comprises *Sambucus nigra* L. with a solvent consisting of ethanol and water,
   b) separating the solvent from the plant material to obtain an extract and
   c) hydrolytically treating the extract of part (b) with hydrochloric acid having a concentration of 1 M to 10M at 80° C. to 100° C. for 30 minutes to 120 minutes.

2. The hydrolysate according to claim 1, wherein the extract is produced from the plant material using an extraction agent made of 50% by volume ethanol and 50% by volume water over 6 hours to 36 hours, while stirring and subsequent vacuum evaporation of the solvent.

3. The hydrolysate according to claim 1, wherein the hydrolytic treatment of the extracts is carried out in the presence of ethanol or ethanol diluted with water.

4. A hydrolysate according to claim 1, wherein preparation of the hydrolysate further comprises evaporating the hydrolytically treated extract to dryness for producing a dry extract and optionally neutralizing.

5. The hydrolysate according to claim 1, wherein the *Sambucus nigra* L. is *Sambucus nigra* L. blossoms.

6. A hydrosylate according to claim 1, wherein thy hydrolysate exhibits an antibacterial effect.

7. The hydrolysate according to claim 6, wherein the antibacterial effect is effective against skin, ENT and respiratory tract bacteria.

8. The hydrolysate according to claim 7, wherein the bacteria are selected from the group consisting of *Staphylococcus aureus* (ATCC 25923), *Staphylococcus epidermidis* (ATCC 12228), *Streptococcus pneumoniae* (DSMZ 20566), *Streptococcus pyogenes* (DSMZ 20565), *Haemophilus influenzae* (DSMZ 4690); *Enterococcus casseliflavus* (DSMZ 20680); *Pseudomonas aeruginosa* (ATCC 27853); *Klebsiella pneumoniae* (ATCC 13883); *E. coli*; *Enterococcus faecalis*; and mixtures thereof.

9. A hydrolysate according to claim 1, wherein the hydrolysate is effective for the protection and/or treatment of infections, orally or topically, on the skin and mucous membranes and is in the form of a galenic formulation.

10. An oral formulation comprising the hydrolysate according to claim 9, wherein the oral formulation is in the form of sugar-coated tablets, tablets, film-coated tablets, capsules, liquid dilutions, drops, oral solutions or syrups.

11. An article used for topical applications comprising the hydrolysate according to claim 9, wherein the article is a spray, ointment, emulsion, powder, liquid or solid preparation for inhalation, compress, wound, dressing gum dressing, tamponade, tonsil brush solution, gargling solution, or rinsing solution for the nose and ears.

12. A tamponade used for dental applications, further comprising the hydrolysate according to claim 9.

13. The formulation according to claim 11, wherein the rinsing solution for the nose and ears is present in combination with physiological or hyperosmolar concentrations of salts or salt mixtures.

14. The hydrolysate according to claim 1, wherein the hydrolysate is in the form of a lyophilisate.

15. An antibacterial agent, comprising a hydrolysate according to claim 1.

16. The antibacterial agent according to claim 15, comprising a pharmaceutically acceptable adjuvant.

17. A retard formulation comprising the antibacterial agent according to claim 15.

18. An oral formulation comprising the hydrolysate according to claim 9, wherein the oral formulation is in the form of drops, oral solutions or syrups.

* * * * *